United States Patent [19]
Mottram et al.

[11] Patent Number: 5,697,326
[45] Date of Patent: Dec. 16, 1997

[54] EXAMINATION OF RUMINANT ANIMALS

[75] Inventors: Toby Trevor Fury Mottram, Chard; Arthur Leonard Wilkin, Hitchin, both of England

[73] Assignee: British Technology Group Limited, London, England

[21] Appl. No.: 436,312
[22] PCT Filed: Nov. 22, 1993
[86] PCT No.: PCT/GB93/02396
   § 371 Date: May 19, 1995
   § 102(e) Date: May 19, 1995
[87] PCT Pub. No.: WO94/12022
   PCT Pub. Date: Jun. 9, 1994

[30] Foreign Application Priority Data

Nov. 20, 1992 [GB] United Kingdom ............... 9224404

[51] Int. Cl.⁶ ........................................... A01J 7/00
[52] U.S. Cl. ............... 119/174; 119/14.47; 119/14.14
[58] Field of Search ..................... 119/174, 14.08, 119/14.02, 14.14, 14.47, 420

[56] References Cited

U.S. PATENT DOCUMENTS 3,022,766   2/1962   McKinley ................ 119/14.47
5,042,501   8/1991   Kenny et al. ............ 128/719
5,047,214   9/1991   Fukui et al. ............ 422/98

FOREIGN PATENT DOCUMENTS

4025404 A   2/1992   Germany ................. 119/174

Primary Examiner—Robert P. Swiatek
Assistant Examiner—Yvonne R. Abbott
Attorney, Agent, or Firm—Cushman, Darby & Cushman IP Group of Pillsbury, Madison & Sutro LLP

[57] ABSTRACT

A method for the examination of the condition of a ruminant animal including sampling odours from at least one part of the animal with an olfactory sensor thereby to identify specific aspects of the animal condition.

21 Claims, 1 Drawing Sheet

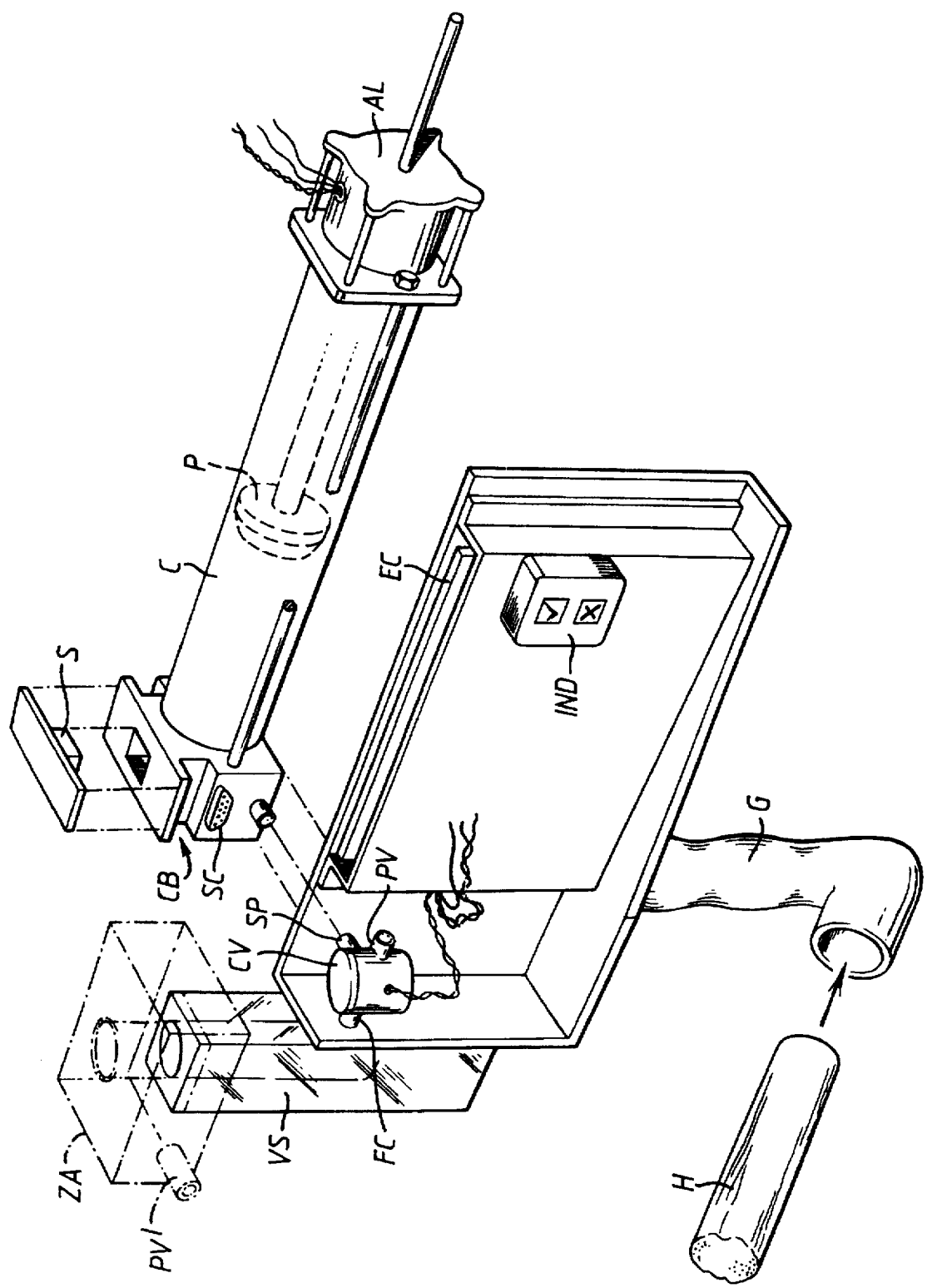

EXAMINATION OF RUMINANT ANIMALS

This invention relates to the examination of ruminant animals and more particularly to the examination of the teats and general condition of ruminant animals kept for milk.

The teats of a milking animal need careful attention to determine that a teat is clean and healthy before milk is drawn from the teat, whether by manual or automatic methods. The routine washing of teats before milking is now considered more likely to increase rather than decrease damage and cross-infection, particularly if the teats are generally clean. Other aspects of animal health also need to be examined and the time of presentation for milking is convenient for this. Ruminant animals not in milk or not kept for milk also need to be examined for general health.

There is therefore a need for a reliable technique for the general examination of ruminant animals.

It is an object of the invention to provide a technique for the examination of the condition and health of a ruminant animal and more particularly one which can be applied in milking animal husbandry whether as part of a manual or automatic milking regime or independently.

According to the invention there is provided a method for the examination of the condition of a ruminant animal including sampling odours from at least one part of the animal with an olfactory sensor thereby to identify specific aspects of the animal condition.

According to an aspect of the invention there is provided a method for the examination of a teat of a milking animal including establishing an examination region in the air around a teat to be examined, purging the region, drawing a sample of air from the region, applying the sample to a sensor and providing a sensor output indicative of any response of the sensor to said sample.

The invention also provides an apparatus to examine a teat of a milking animal including an examination device to receive a said teat, means to purge the examination device, means to support the device with said teat received therein, means to draw a sample of air from around the teat received in the device, means to apply said sample to a sensor and means to supply a sensor output indicative of sensor response to said sample.

The examination device may be an open-top vessel into which a teat can be inserted. The device may be a teat cup like structure.

The purging is arranged to at least reduce the inclusion of general ambient air in the sample, ensuring that the sample is representative of material diffusing from the teat or other part of the ruminant animal or a substance thereon. The purging air may be used as a reference for the sensor before a sample is taken. Purging air may be supplied selectively to the top and the bottom of the device. The purging may be by a flow of clean air, for example from a pressure bottle. The purging and sampling action may be controlled by a changeover valve. The sample may be drawn by a piston and cylinder arrangement operated by a lead screw actuator to enable a precise sample size. The purge air may drawn into a sample chamber then expelled to purge the region by the action of the piston and cylinder arrangement. The purge air and sample may flow in the same direction. The purge air and sample may be drawn past a sensor by suction.

The sensor is conveniently one commonly called an electronic "nose", that is an olfactory sensor. Such a sensor can be based on a conducting polymer, a metal oxide or other sensing material for olfactory purposes, with associated electronic signal processing circuitry.

The sensor can be arranged to sense diffusion from the teat or another part of the animal or a substance thereon of organic material characteristic of one or more of faecal material, blood, earth, the state of the metabolic process and the conditions of oestrus of ketosis.

The method and apparatus may be arranged for operation manually by an operator or in response to a control instruction by a robot. Such a robot may be part of an automatic milking apparatus. The examination may be applied when an animal presents for milking. The examination may be carried out in a milking stall before a milking apparatus is applied to a teat. The examination may be carried out before an animal is permitted to enter a milking stall. In response to a sensor output indication of teat condition unsuitable for milking the examined teat may be washed and again examined. If an animal on examination has an unsuitable teat condition it may be directed away from a milking stall to an area for further examination.

The apparatus, where in contact with the sample, is of an inert material. Conveniently this is polytetrafluorethylene.

The apparatus may be fixed to an animal stall or the like where diffusion, exhalation or other evacuations of the ruminant animal are present for examination.

Embodiments of the invention will now be described with reference to the accompanying drawing which is a perspective view of an apparatus according to the invention.

The apparatus shown in the drawing includes an examination device in the form of an open-top vessel VS to receive a teat of a milking animal and provide around a received teat a region which can be purged by an air flow and from which a sample of air can be drawn. A flow connection FC is provided at the lower, closed, end of the vessel. The flow connection is controlled by a valve CV which can be selectively operated to allow entry of pure air through one valve port PV and to allow extraction of sample air via FC through another valve port SP. A pressure bottle of pure compressed air or other gas (so-called zero air) is connected to the port PV. To the other port SP a piston and cylinder arrangement is connected with the connection to the cylinder offset to cause swirl in flow into the cylinder.

The piston P is drivable to and fro in the cylinder C in controllable manner by an actuator AL. A sensor S is placed on a coupling block CB to be exposed to the sample drawn into the cylinder. The sensor is conveniently of the olfactory type, available commercially in various forms and commonly called an electronic "nose". An electronic circuit EC, connected via connector SC, is arranged to provide an indication of the response of the sensor at an indicator IND and over an output connection. The electronic circuit can also be arranged to control the valve and piston actuator and the operating cycle of the apparatus. Power also can be supplied through this connection. The exact form of the electronic circuit will be appropriate to the sensor used and the manner in which the indication is to be applied. Suitable electronic circuitry will be readily apparent to those skilled in the art.

In operation the vessel is purged by a flow of air from the pressure bottle, either before being placed around the teat or when the teat is in place, the purge flow being controlled by the valve. In one arrangement the purge air flows through the valve into the cylinder with the piston withdrawn and is then sent to the vessel through the valve by operating the piston. A sample is then drawn from the space around the teat by operating the valve to connect the space to the piston and cylinder, if not already so-connected, and again withdrawing the piston along the cylinder. The offset flow connection encourages a swirl in air movement in the cylinder.

The response of the sensor to the sample is derived by the electronic circuit and an output indication provided. After examination of a sample the piston and cylinder and sensor can also be purged by pure compressed air. A dwell time may be needed for the proper response of the sensor. The profile of the sensor response as the sample is drawn past may be significant as the proportion of material may vary during the sample flow.

The parts of the apparatus in contact with the sample must not cause contamination of the sample, for example by retaining part of an earlier sample or by releasing material into the sample. Polytetrafluoroethylene (ptfe) is a suitable substance for such parts of the apparatus.

In a specific form of the apparatus the control valve is a 3-way TEFLON (RTM) valve supplied by NResearch of New Jersey USA, which is operated at 12V dc. The piston and cylinder are made from ptfe with an O-ring to seal the piston to the cylinder. The O-ring must not release or retain sample material. The piston is operated by a stepper motor lead screw actuator of the AIRPAX (RTM) type L92211-P2, operated at 12V dc. Such an actuator can provide a very precise drive of the piston at a selected speed so that the sample and purge volume can be accurately set. Conveniently the purge volume is greater than the sample volume and the cylinder is sized for the purge volume.

It is important that the sample does not include air from other than the region around the teat. If air from outside this region is included in the sample false results may be obtained. The teat may bring with it stray "odours" and the purging action is therefore preferably carried out with the teat in the vessel. The vessel VS must, of course, be clean to avoid false results. A check may be made of the empty vessel between tests. The vessel could be routinely cleaned at each test.

The apparatus can be hand-held (grip G) or supported by a shaft (H) or other means, for example on a milking robot such as is described in UK patent publication 2226941, incorporated herein by reference.

The handling of the animal after examination is determined by the indication of the sensor response so as to be milked, have a cleaning action carried out or be directed to another area for further examination.

In another form of the apparatus the flow route is of different form. A further supply of zero air as purge air is introduced at port PV' of additional unit ZA at and around the top of the examination device, such as vessel VS, into which the teat is received. In this way the drawing in of ambient air, with the possibility of bringing in stray odours, is further reduced. The flow route is now always in the same direction, as explained below. The flow path at the sensor S is preferably such as to produce a flow across the sensor rather than allow a volume of gas to collect around the sensor. Sensors for humidity and temperature of the flow are also fitted here. The piston and cylinder arrangement is operated to bring about the required flow rate along the flow route. It is possible to use suction from some external source, such as the vacuum of a milking apparatus (not shown), as an alternative to the piston and cylinder although some indication of flow rate may be needed to enable consistent sensor results. The lower part of the vessel VS can be openable to aid cleaning. It may be sufficient to line the vessel and other parts with ptfe. Zero air may also be selectively supplied directly to the piston and cylinder arrangement and extracted therefrom as a purging action. The exact physical form of the apparatus can be altered to suit a chosen component selection or other constraint as will be apparent to those skilled in the art and in accordance with the precautions indicated.

In operation of the form of the apparatus just described at the beginning of an examination the purge supply of air or other gas, such as the so-called zero gas, is made available at port PV'. The piston P is positioned in the cylinder end close to the sensor. Before the introduction of a teat for examination into the vessel VS the purge supply at PV' is started. With the teat in place, or earlier if required, the valve CV is operated as above to supply zero air which, by slow movement of the piston along the cylinder, is drawn over the sensor S.

When the purge is effective the valve CV is operated and the purge supply to the sensor replaced by the zero air and any odours from the vessel VS where the teat is in place. The movement of the piston is continued. This brings about the flow of zero air past the teat in vessel VS and draws odours from the teat past the sensor S so that significant odours can be assessed and indicated as before.

In a further form of the apparatus a teat-cup like examination device is fitted with an olfactory sensor. Gas flow paths are provided to the top and bottom of the teat-cup like device, the flow path to the bottom of the device including the sensor. Zero air can be selectively supplied to each flow path. The top flow path conveniently discharges around the top of the device. Suction can be selectively applied to the flow path to the bottom of the device.

In operation of this further form zero air is firstly caused to flow along the flow path to the bottom of the device, past the sensor, and then up through the device and out the open top, past a teat in place in the device. This zero air flow is used to calibrate the device as well as purge any stray odours. The zero air supply is then transferred to the flow path to the top of the device and suction applied to the flow path extending to the bottom of the device. Zero air is thus drawn past a teat in the device and then past the sensor for the sensor to respond to any odours swept along with the zero air flow past the teat. Suitable valves or other flow control and electronic circuit arrangements will be apparent to those skilled in the art having regard to the descriptions above. A suitable seal, operated by differential pressure, may be provided at the top of the device so that the purge air flow can escape, the seal being open, while when suction is applied the seal operates so that only zero air from the top flow path passes the teat and ambient air cannot enter. The guidance above on materials and cleaning applies to this further form of the apparatus.

Reference has been made above to the nature of response by the sensor. Typical response by the sensor is for a significant resistance change to occur over a period of about ten seconds starting some five seconds after the flow of the sample from the space around the teat. When cow faecal material is present on the teat the sensor resistance change is about twice that when faecal material is not present. The change of the sensor resistance generally reduces again as the flow continues, for both clean and dirty teats. Relative humidity and temperature can affect the sensor response and these can be sensed so that the olfactory sensor response can be properly interpreted by the electronic circuitry. It may be necessary to make some "trial" runs of the apparatus before actual use to ensure that a proper reference condition has been established for a particular combination of humidity and temperature.

It is desirable to achieve as long a life as possible from the olfactory sensor. These sensors can deteriorate due to contamination and can "drift" if sensed materials are retained. For these reasons it is desirable to maintain the sensor in clean air except when in use. The purge supply can be arranged to do this without excessive consumption.

As described above the teat to be examined is received into a device such as a vessel. In another embodiment a vessel is not used and a structured air flow can be used to direct air which may carry significant odours from an area of interest of an animal to the sensing apparatus. The purge action can be provided by the structured flow.

Examination of the exhaled breath from the respiratory tract of a ruminant can be used instead of a blood test,for certain conditions. A blood test involving taking a blood sample and then analysis for each animal is expensive and, because it is invasive, unattractive. By capturing exhaled breath from the nostrils of a ruminant animal and examining this for odours, useful information can be acquired. Purging, as mentioned above, is needed and any collection device needs to be a close fit to the nostrils of the animal.

As the breath examination can be done regularly and frequently without professional intervention, such as is required for a blood test, it is relatively cheap and can be carried out at milking time and used as a control input for a milking regime control system, relating to feeding, milking and other aspects of the regime.

The invention also provides general sensing of an animal condition by examination of a sample, such as a sample of breath, by apparatus including an olfactory sensor for conditions such as oestrus and ketosis. Appropriate modifications for the apparatus will be apparent to those skilled in the art. Diffusion, exhalations or other evacuations of a ruminant animal can also be sensed. The apparatus may be fixed to a stall where the breath or other odour of the animal or animal waste products is likely to be present, for routine testing. Various conditions of the animal may tested including metabolism and these tests are relevant to ruminants in general, whether kept for meat or milk purposes.

We claim:

1. A method for the examination of a condition of a ruminant animal comprising sampling odors from at least one part of the animal with an electronic olfactory sensor thereby identifying a specific aspect of the animal's condition, including establishing an examination region in the air around a part of the animal to be examined, purging the region, drawing a sample of air from the region, applying the sample to the sensor and providing a sensor output indicative of any response of the sensor to said sample which determines whether the animal is to be one of milked, cleaned or examined further.

2. A method according to claim 1 including providing the examination region as a vessel to receive a teat.

3. A method according to claim 1 including providing the examination region as a structured air flow.

4. A method according to claim 1 including examining the condition of a milking animal presenting for milking and controlling the progress of the milking process thereafter in dependence on the identified condition of the animal.

5. A method according to claim 4 including examining the animal before entry to a milking position.

6. Apparatus for examining the condition of a ruminant animal comprising means for establishing an examination region in air around a part of the ruminant animal to be examined, means for purging the region, means for drawing a sample of air from the region, means for applying said sample to an electronic olfactory sensor and means for supplying a sensor output indicative of the condition present in the animal.

7. Apparatus according to claim 6 in which the examination device is an open-top vessel into which a teat can be inserted.

8. Apparatus according to claim 6 in which the examination device is a teat-cup like structure.

9. Apparatus according to claim 6 in which the purging is arranged to at least reduce the inclusion of general ambient air in the sample, ensuring that the sample is representative of material diffusing from the teat or other part of the ruminant animal or a substance thereon.

10. Apparatus according to claim 6 in which the purging air is a reference for the sensor before a sample is taken.

11. Apparatus according to claim 6 in which the sensor is based on a conducting polymer, a metal oxide or other sensing material for olfactory purposes, with associated electronic signal processing circuitry.

12. Apparatus according to claim 6 in which the sensor is arranged to sense diffusion from the teat or another part of the animal or a substance thereon of organic material characteristic of one or more of faecal material, blood, earth, the state of the metabolic process and the conditions of oestrus or ketosis.

13. Apparatus according to claim 6 arranged for manual operation by an operator.

14. Apparatus according to claim 6 arranged for operation by an automatic milking apparatus.

15. Apparatus according to claim 6 including means to control a sequence of operations including a purge operation and a sample taking operation.

16. Apparatus according to claim 6 including means to cause flow of said purge and said sample and means to control the means to cause said flows.

17. Apparatus according to claim 6 including means to collect breath or other flow containing an odor of the animal as a sample, means to purge said collecting means, sensing means to receive said sample and identify at least one specific condition of the animal and means to supply an indication of said condition being present.

18. Apparatus according to claim 6 arranged to sense for at at least one of the conditions ketosis and oestrus.

19. Apparatus according to claim 17 arranged for mounting on a stall for a ruminant animal.

20. Apparatus according to claim 6 arranged to produce a structured air flow to collect an odour.

21. An apparatus according to claim 6, wherein said sensor output indicates whether the animal should be milked, cleaned or examined further.

* * * * *